United States Patent
Eley

(12) 
(10) Patent No.: US 6,200,590 B1
(45) Date of Patent: Mar. 13, 2001

(54) CONTROLLED, PHASED-RELEASE SUPPOSITORY AND ITS METHOD OF PRODUCTION

(75) Inventor: John Graham Eley, Alabaster, AL (US)

(73) Assignee: Naphcare, Inc., Birmingham, AL (US)

( * ) Notice: Subject to any disclaimer, the term of this patent is extended or adjusted under 35 U.S.C. 154(b) by 0 days.

(21) Appl. No.: 09/131,591

(22) Filed: Aug. 10, 1998

(51) Int. Cl.$^7$ .................................................. A01N 43/22
(52) U.S. Cl. .................. 424/433; 424/434; 424/DIG. 15; 514/965
(58) Field of Search ..................... 424/433, 434, 424/DIG. 15; 514/965

(56) References Cited

U.S. PATENT DOCUMENTS

| | | | |
|---|---|---|---|
| 4,652,441 | 3/1987 | Okada et al. | 424/19 |
| 5,215,758 | 6/1993 | Krishnamurthy | 424/488 |
| 5,500,221 | 3/1996 | Murata et al. | 424/436 |
| 5,518,730 | 5/1996 | Fuisz | 424/426 |
| 5,985,313 | * 11/1999 | Neurath et al. | 424/434 |

OTHER PUBLICATIONS

E. Allemann, et al., "International Journal of Pharmaceutics", vol. 87, pp. 247–253 (1992).

* cited by examiner

*Primary Examiner*—Carlos A. Azpuru
(74) *Attorney, Agent, or Firm*—Wm. Randall May

(57) ABSTRACT

A phased-release suppository delivery system is disclosed wherein microscopic polymeric "nanospheres" ladened with one or more active agents are homogeneously incorporated within a pharmaceutically acceptable suppository base. The preparation of the "nanospheres" allows the spheres to be transported, substantially intact, across fenestrated membranes such as the capillary membranes of the rectum. The method of preparation of the "nanospheres" allows for the controlled release of active agent(s) only after a substantial number of the spheres have been transported across the capillary membrane of the rectum or other body cavity and have been taken up into the systemic circulation system.

8 Claims, 5 Drawing Sheets

Stage 1 - Method of Preparation of Nanospheres Containing a Drug

Stage 1 - Method of Preparation of Nanospheres Containing a Drug

Alternative Method for Production Nanospheres (Salting Out)

CONTROLLED, PHASED-RELEASE SUPPOSITORY AND ITS METHOD OF PRODUCTION

BACKGROUND OF THE INVENTION

This invention relates generally to suppository preparations and more specifically to a phased, systemic-delivery suppository preparation and its method of production.

As is well known, suppositories are medicated dosage forms inserted into body cavities such as the rectum, urethra, or vagina for the eventual delivery of one or more active agents to the systemic circulation and/or to local tissues. Suppositories are valuable, and often critical, additions to the symptom control armamentarium. This is especially true for those patients who, due to advanced disease, advanced age, nausea or other physiological or neurological problems, are unable to receive medications orally, intravenously or by injection. The problem is even more critical for the terminally ill patient who suffers from intense, intractable pain. Suppository dosage forms of medications presently being given to patients, particularly in the control of pain, are often times irregular in the delivery or bioavailability of the administered agents with the delivery of medications sometimes oscillating between levels which are far below the effective pain relieving dose to near toxic levels.

In recent years, prescribers have increasingly requested that pharmacists prepare extemporaneous suppository dosage forms for symptom control medications. However, because these dosage forms are not commonly compounded today, many prescribers who order drugs, the pharmacists who compound them, and the nurses who administer them, are unfamiliar with the criteria for properly formulated suppositories. Moreover, while suppository dosage forms have been formulated in the past for many agents, often the duration of the action of the drug is relatively short, requiring frequent administration thereby making usage inconvenient and/or ineffective. Attempts have been made, with limited success, to produce suppositories that are capable of delivering medications in a sustained or controlled release manner. Major obstacles include erratic absorption as herein described, and the timing of evacuations of the particular body cavity chosen for insertion. Many drugs can be delivered by the use of suppository dosage forms but the controlled release of such drugs has yet to be refined. Methods to prolong the action of drugs in a suppository sustained release form are therefore needed and desired.

Use of microparticles as a delivery system for drugs in clinical situations has been proven to be viable for many years. Since the advent of liposomes in the seventies, science has advanced to the point where many pharmaceutical materials are employed either singularly or in various percentages to produce optimum release rates for drugs or proposed drugs. However, prior art suppository preparations will typically release their active agents within the lower rectum thereby limiting the bioavailability of the agents. Substantial release of the active agent of the suppository into the lower rectum can and does limit the percentage of agent which can actually reach the systemic circulation system where it is needed.

It would be expedient, therefore, for the provision of a suppository formulation which will give more control over the release and bioavailability of medications. Furthermore, suppository preparations which are capable of releasing substantially all of their active agent(s) directly into the patient's systemic circulation instead of the lower rectum would greatly enhance the bioavailability and usefulness of such dosage forms and would substantially eliminate the problems associated with the untimely evacuation of the body cavity chosen for insertion.

The present inventor, through extensive experimentation and study, has developed a phased-release suppository delivery system incorporating a novel method of producing drug-ladened, polymeric "nanospheres" within a suppository base. The method of preparation of the "nanospheres" allows for the release of their active agent(s) only after a substantial number of the spheres have been transported across the capillary membranes of the rectum or other body cavity and have been taken up into the systemic circulation system. A small number of the spheres will inevitably become lodged within the mucus membrane of the chosen body cavity, however, even these spheres will, upon dissolution, release their active agent(s) from said area over an extended period of time.

SUMMARY OF THE INVENTION

In view of the foregoing, it is a primary object of this invention to provide a phased-release suppository preparation and delivery system which incorporates microscopic, drug-ladened, polymeric nanospheres within a homogenous suppository base.

According to an embodiment of the invention, a phased-release suppository delivery system comprises a novel method of producing polymeric nanospheres ladened with one or more active agents wherein the nanospheres are homogeneously incorporated into a pharmaceutically acceptable suppository base. The release of one or more active agents contained within the suppository nanospheres is controlled according to a four-phase delivery system. The first phase comprises the delivery of the suppository dosage form into the rectal cavity (or other body cavity); the second phase is the release, upon aqueous solubility of the suppository base, of the polymeric nanospheres into the mucosa of the chosen body cavity; the third phase is the uptake of nanospheres into fenestrated capillaries of the chosen cavity; and, the fourth phase comprises release of active ingredient(s) directly into the patient's systemic circulation upon dissolution of the polymeric nanosphere vehicles. The release of the active ingredient(s) of the nanospheres is controlled by the percentage composition of the polymer(s) used to produce the spheres.

An important advantage of the present invention is the provision of methodology for the production of a controlled, phased-release suppository preparation comprising substantially spherical microscopic particles consisting of a matrix of one or more active agents within a polymeric carrier. Said matrix forming a homogeneous, microscopic delivery system capable of being transported, substantially intact, across capillary membranes and into the systemic circulation system.

Another advantage of the present invention is the provision of methodology necessary to produce drug-ladened nanospheres no larger than 300 nanometers in diameter.

Another advantage of the present invention is the provision of a homogeneous suppository preparation containing drug-ladened nanospheres which will release their active agent(s) only after a substantial number of the spheres have been transported across fenestrated capillary membranes and have been taken up into the systemic circulation system.

A further advantage of the present invention is the provision of a homogeneous suppository preparation containing nanospheres wherein one or more active agents and polymers are caused to form a matrix whereby the agents are uniformly distributed throughout the nanosphere particle.

Another advantage of the present invention is the provision of a controlled release suppository preparation which can accommodate both water soluble and lipid soluble agents.

Another advantage of the present invention is the provision of a controlled release suppository preparation comprising a delivery system which provides for longer lasting action of its active agents.

A further advantage of the present invention resides in the bioavailability of the active agent(s) contained within the nanosphere matrix which is controlled by the percentage of polymers used to form the nanospheres.

Another advantage of the present invention is that any nanospheres which become lodged within the mucosa of the chosen body cavity will also release their active agent(s) from that area over an extended period of time.

A further advantage of the present invention is the provision of a phased release suppository preparation which is not an encapsulation and wherein one or more active agents are contained within a polymeric preparation as a homogeneous matrix.

A further advantage of the present invention is the provision of a phased delivery, controlled release suppository preparation which requires no pH adjustments, cross-linking agents or buffering agents in order to control the release rate of its active agent(s).

DETAILED DESCRIPTION

Figure 3:
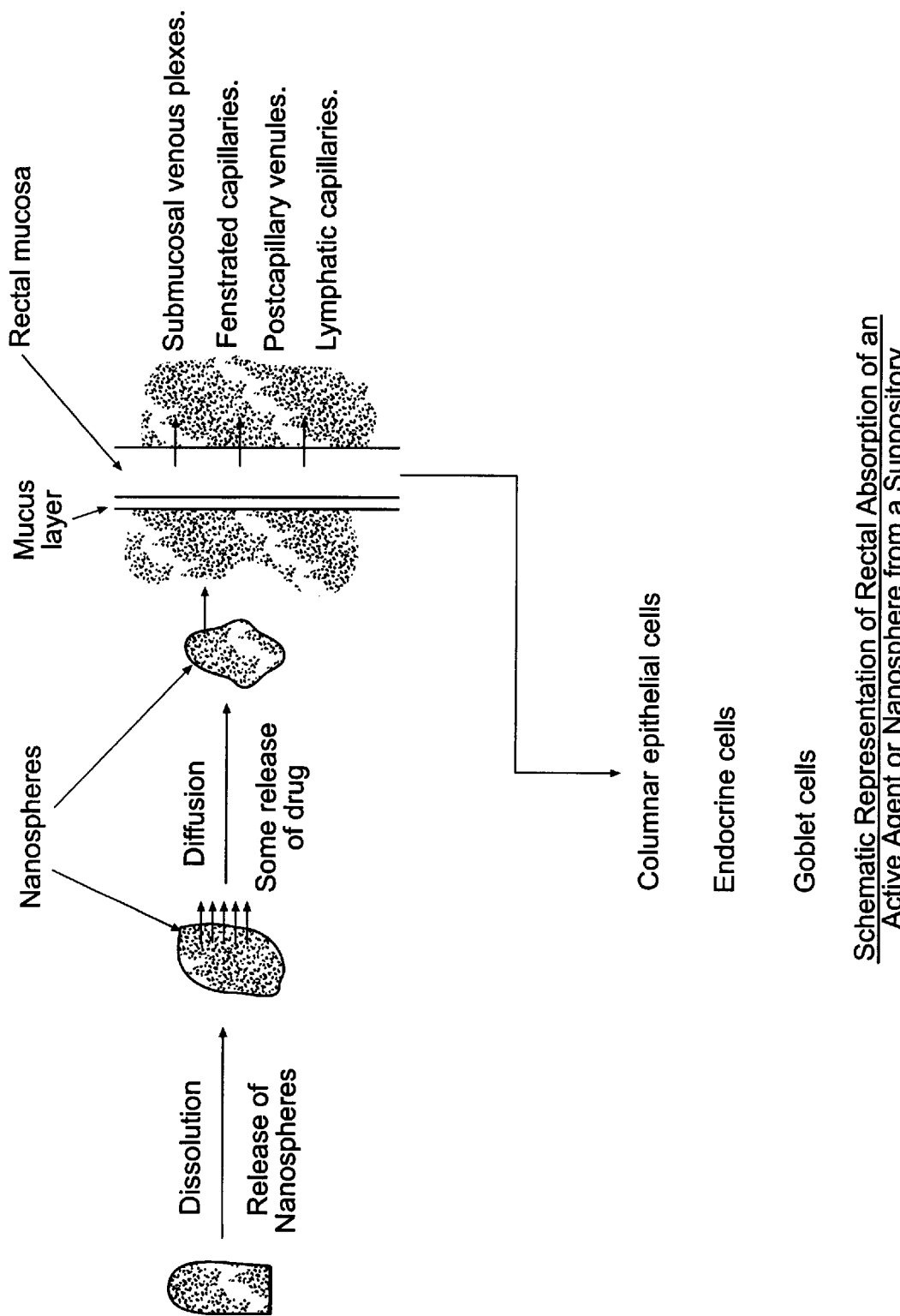
FIG. 3 is a schematic representation of rectal absorption of nanospheres from the inventor's suppository preparation.
Figure 4:
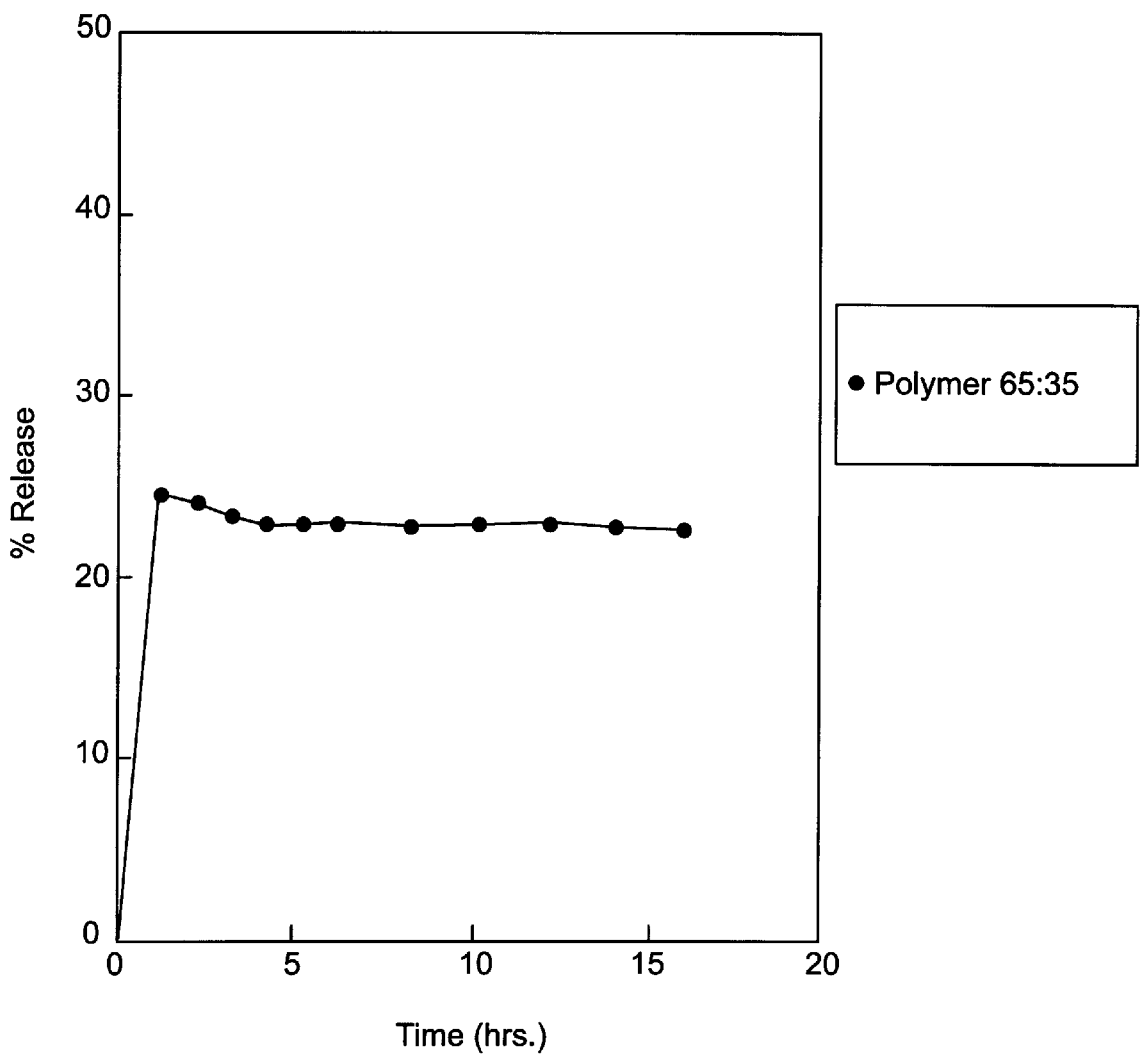
FIG. 4 shows the dissolution profile of suppositories of the present invention containing nanospheres ladened with morphine sulfate as the active ingredient.
Figure 5:
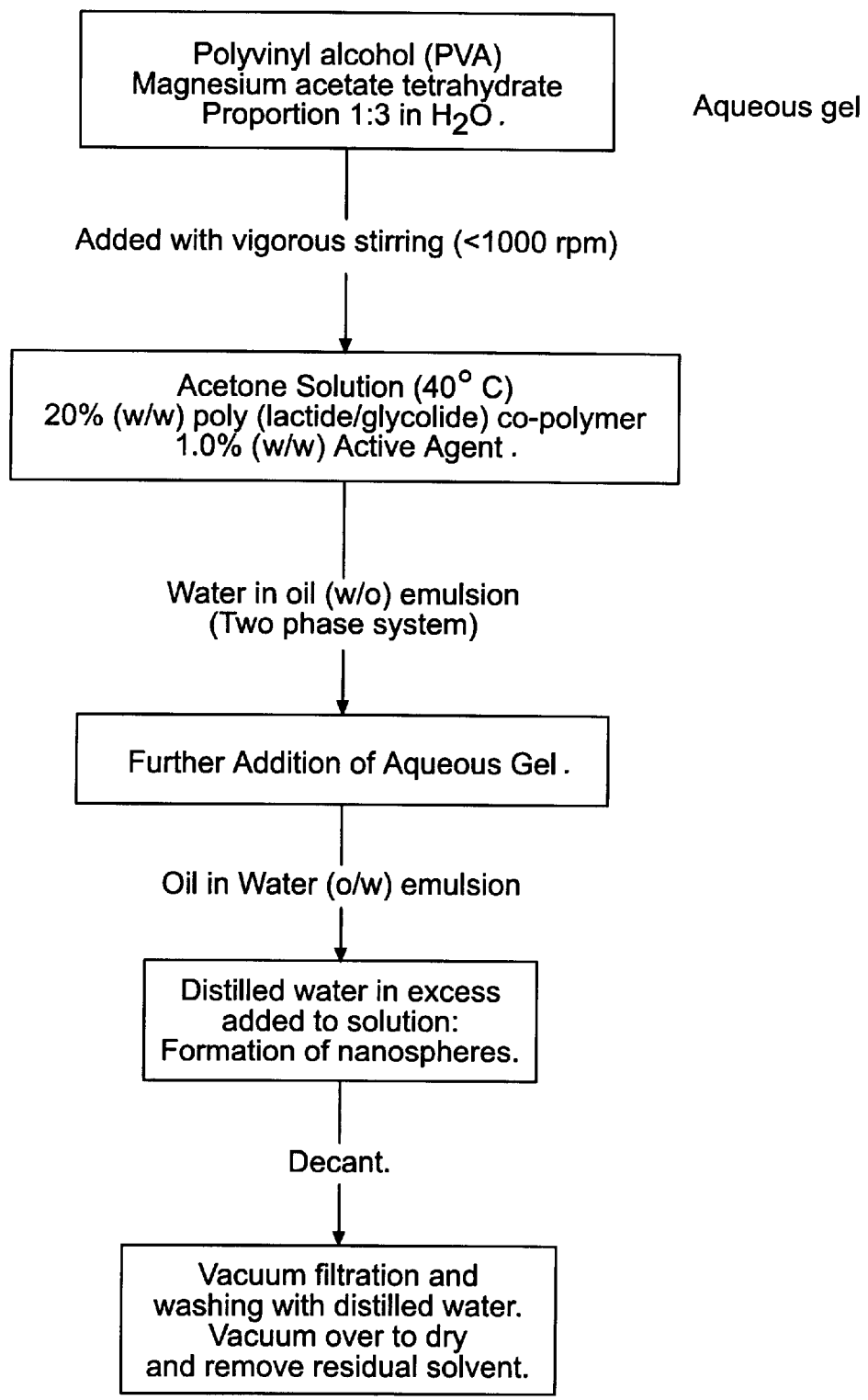
FIG. 5 is a flow diagram detailing an alternate method of preparation of nanospheres containing one or more active agents.

There is no known limitation as to the kind or number of drugs or active agents that can be used with the present invention. However, by way of example, the drug "morphine sulfate" will be used as the active agent in this description of the best mode for conducting the invention. The invention, as previously described and as shown in the schematic representation of FIG. 3, suggests a double-delivery system with a four phase release of drug or active agent. The double delivery system comprises one or more active agents in a polymeric nanosphere matrix vehicle within a suppository base. The four phase release consists essentially of the delivery of the whole system as a suppository to the rectal, or other, body cavity; the release, upon the aqueous dissolution of the suppository base, of the polymeric nanospheres into the chosen body cavity; the uptake of nanospheres into fenestrated capillaries of the chosen body cavity; and, the controlled release of the drug(s) or active agent(s) into the systemic circulation system. As previously discussed, one of the primary advantages of the present invention and its method of production is that the drug-ladened polymeric nanospheres are formed as a matrix and, when properly produced as outlined herein, will not release their active ingredient(s) until a substantial number of the spheres have been transported across the capillary membranes and taken up by the systemic circulation system. Furthermore, any nanospheres which become lodged within the mucosa of the chosen body cavity will also release their active ingredient(s) from said area over an extended period of time.

A suppository base comprised of polyethylene glycols (PEGs) is the proposed vehicle for delivery of the polymeric, drug-ladened nanospheres. However, virtually any base component which will dissolve upon contact with the body fluids of the chosen cavity for insertion of the suppository can be used. Examples of other suppository base components which could be used to provide a proper vehicle for the delivery of the polymeric nanospheres include cocoa butter, glycerinated gelatin, hydrogenated vegetable oils, fatty acid esters of polyethylene glycols, glycolsurfactant PEGs, and nonionic surfactant materials such as polyoxyethylene derivatives of sorbitan monostearate and polyoxyl—40 stearate.

As stated, PEGs are the preferred suppository base vehicle for the delivery of the co-polymer nanospheres to the chosen body cavity. As is well known, PEGs are polymers of ethylene oxide and water which can be prepared to various chain lengths, molecular weights and physical states. Various combinations of PEGs may be prepared by fusion in order to obtain a range of different melting points. However, since PEGs dissolve upon contact with body fluids and do not dissolve at body temperature, there is no dependence upon a melting point at or near body temperature and problems associated with handling and storage are greatly simplified.

Figure 2:
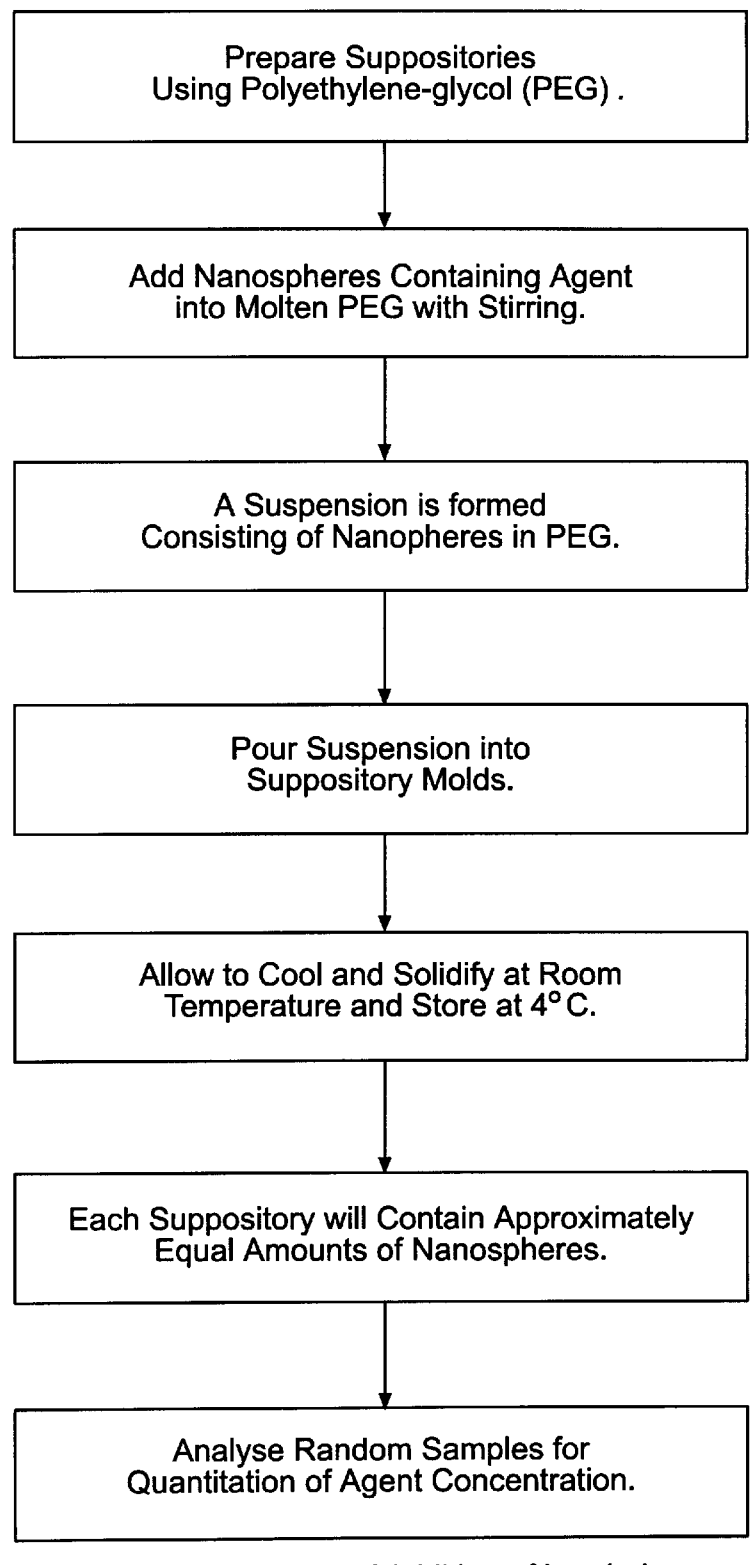
FIG. 2 is a flow diagram detailing the inventor's method of adding the drug-ladened nanospheres to a suppository base.

The PEG suppository base components used in this preferred embodiment are produced by a typical fuse-melt or melt-molding method. The drug-ladened, polymeric nanospheres of the invention are added to the suppository base component in a molten state and the method of production, as shown in the flow diagram of FIG. 2 and as detailed hereinafter, causes the spheres to be evenly distributed throughout the suppository.

Figure 1:
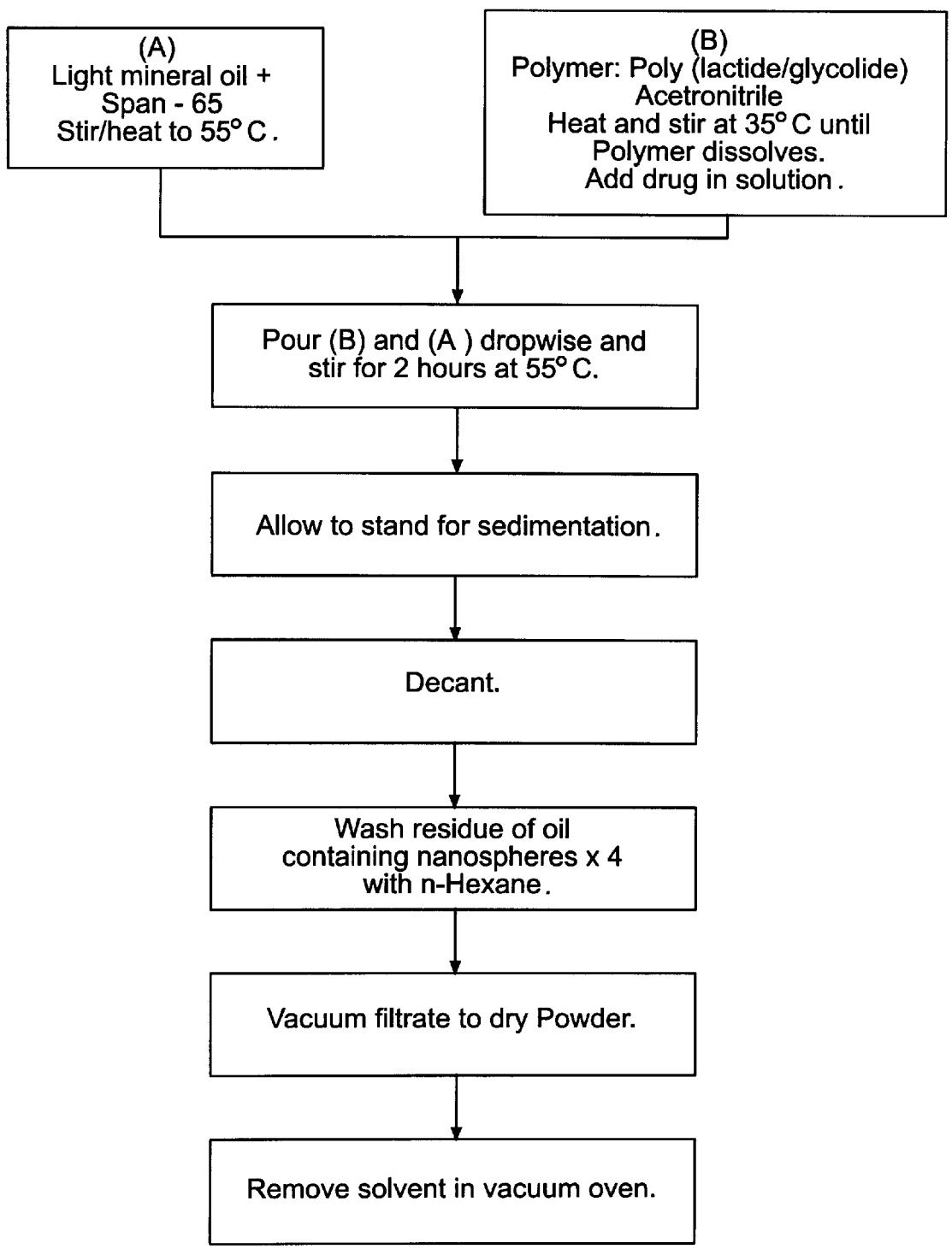
FIG. 1 is a flow diagram detailing the method of preparation of nanospheres containing one or more active agents.

Generally, as shown in the flow diagram of FIG. 1, the nanospheres of the present invention are produced by a water-in-oil method whereby polymer is dissolved in acetonitrile or similar solvent and one or more drugs or active agents are added. The synthetic co-polymer "polylactide-glycolide)" is the preferred delivery vehicle for the nanospheres, however, other synthetic and natural biodegradable polymers could be used with varying results. Examples of natural biodegradable polymers include serum albumins, collegen, gelatin, hemoglobin, polysaeccharides, dexoyglucopyranose and celluloses. Examples of other synthetic biodegradable polymers include poly(alkyl-a-cyanoacrylates), poly(amides), poly(acrylamide)-hydrogers, poly(orthoesters), poly(amino acids), poly(urethanes), polyacrylates/polymethacrylates, polyanhydrides, polyglycerol esters, polyhydroxybutyrate, polyhydroxyvalerate, poly-e-prolactone, polystyrene and co-polymers of styrene, polyethylenimine, polydimethyldiallylammonine chloride, glutamic acid—ethyl glutamate co-polymers, isocyanates, caboxyvinyl, polycritic acid, polymalic acid, poly-β-hydroxybutric acid, poly-alkylene oxalates, poly-orthocarbonate/polycarbonates, silicone, maleic anhydride polymers, ethylene—vinyl acetate co-polymer, polyvinyl alcohol, polyacrylamide and other aliphatic polyesters such as poly(lactic acid), poly(glycolic acid), poly(ε-caprolactone), poly(hydroxy butyrate) and poly(hydroxy butyrate-co-valerate). The amount of drug or active ingredient contained within each suppository will be determined by the concentration of the drug or active ingredient contained within the nanospheres. The concentration of drug or active agent contained within the nanosphere matrix will be formulated during the nanosphere production stage as detailed hereinbelow.

BEST MODE OF CARRYING OUT THE INVENTION

Preparation of a preferred embodiment of the invention is conducted in two stages as outlined hereinbelow:

Stage One

Light mineral oil is poured into a glass beaker and stirred with a double-bladed overhead paddle in a constant temperature water bath (55° C.). Stirring speed will vary depending upon the size of nanospheres desired. A surfactant, (Span-65-4 g) is added to the light mineral oil with continuous stirring at 55° C. for 15–20 minutes until the surfactant has completely dissolved. Polymer, comprising a predetermined ratio of poly(lactide-glycolide) co-polymer, (Birmingham Polymers, Birmingham, Ala. USA) is weighed out (0.5 g) and the polymer is dissolved in acetonitrile solvent (1 ml) while being stirred on a hotplate at 35–40° C. for five (5) minutes. The percentage of lactide to glycolide polymer will determine the rate of dissolution of the nanospheres within the systemic circulation and therefore the release rate of the active ingredient(s) contained within the nanosphere matrix. Upon dissolution of the polymer in the acetonitrile, one or more drugs or active ingredients, such as morphine sulfate (5–10 mg), is dissolved into the minimum amount of water, or other suitable organic solvent, necessary for dissolution while being stirred at ambient temperature. Once dissolved, the morphine sulfate or other drug mixture is added to the polymer solution. A suspension is formed in which the morphine sulfate or other drug mixture is suspended within the dissolved polymer. The resulting mixture is maintained at 40° C. while being stirred. This suspension is then added to the light mineral oil/surfactant solution and allowed to stir for two (2) hours at 55° C. Care must be exercised to ensure the polymer/drug suspension is added to the light mineral oil/surfactant solution in a drop-wise manner before the temperature reaches below 35° C., otherwise there will be a high percentage of solidified drug/mixture remaining in the beaker.

During the mixing procedure, the polymer/drug suspension is forced into spheres by the continuous stirring action of the double-bladed paddle. The surfactant, a surface-active agent, has the effect of preventing the spheres from clumping together. No cover is placed over the glass beaker during the heating/stirring operation in order to allow the acetonitrile solvent to evaporate. However, it should be noted that this process does not remove all of the acetonitrile solvent.

After approximately two (2) hours of continuous stirring, the mixture is allowed to cool and stand over a period of several hours in order to allow sedimentation of the nanospheres to occur. Most of the oil/surfactant mixture is then decanted and discarded leaving the majority of the nanospheres in the residue. The residue containing the nanospheres is then diluted with an alliphatic organic solvent such as n-hexane and filtered under vacuum in order to remove all traces of oil and surfactant. The nanospheres are washed a number of times with n-hexane while being vacuum filtered and are then dried to a powder by air flow. The nanospheres are frequently viewed under a microscope during this process to ensure that all the mineral oil and surfactant has been removed and that there is no adhesion between the nanosphere particles. The resulting product, microscopic spheres containing a homogenous matrix of morphine sulfate and co-polymer, is placed in a vacuum oven and thoroughly dried in order to remove any remaining acetonitrile solvent residue.

Stage Two

A suppository base of Polyethylene-glycol (PEG 8000) is melted in a constant temperature water bath. Once the PEG is in a molten state, the nanospheres produced in the previous stage are added while the suspension is being stirred with a glass rod. The nanospheres form a suspension with the PEG and the stirring action causes them to be evenly and homogeneously distributed throughout the PEG/nanosphere suspension. The molten PEG/nanosphere suspension is then poured into pre-heated metal molds for cooling and solidification. The resulting suppository preparation is allowed to cool and solidify at room temperature and the suppositories are then placed into storage at 4° C. As a result of this process, each suppository will contain approximately equal amounts of nanospheres containing equal amounts of active agent(s) such as morphine sulfate used in this example.

When the suppository preparation is used rectally, the drug-ladened nanospheres will be placed into intimate contact with the rectal mucosa which behaves as a lipoidal barrier and has little buffering capacity. Nanosphere absorption generally takes place through the veins of the inferior part of the submucous plexus which drain into the internal pudendal veins. The nanospheres, due to their size, will generally be taken up by the fenestrated capillaries, the postcapillary venules and the lymphatic capillaries of the rectal mucosa. Once taken up by these capillaries, the nanospheres would be within the systemic circulation and would be able to remain in the blood for an extended time. During this time, dissolution of the co-polymers would occur thereby releasing, over an extended period of time, the active agent contained within the nanosphere/co-polymer matrix. It will be understood that a small percentage of the nanospheres may be unable to pass into the capillary bed of the rectal mucosa for various reasons. However, these nanospheres would still undergo dissolution, dependent on the composition of the co-polymers used to produce them, and would release their active agent(s) over a period of time in excess of that of prior art suppositories. Active agent(s) released by nanospheres which have become lodged within the rectal mucosa will be taken up primarily by the lower hemorrhoidal plexus (as opposed to the middle or higher hemorrhoidal plexeses). This is physiologically advantageous since this route by-passes the portal system thereby avoiding the first-pass mechanism imposed by the liver where much of the agent would be enzymatically reduced before its release into the systemic circulation system.

An alternate method of producing the polymeric, drug-ladened nanospheres of the present invention includes a modified "salting out" process whereby an aqueous gel comprised of water-soluble polymer, such as polyvinyl alcohol, and a salting out agent, such as magnesium acetate tetrahydrate, is dissolved in warm distilled water. Said aqueous gel is added in two stages, under constant vigorous stirring with a turbine propeller, to a solution of acetone or similar solvent containing dissolved polymer and one or more active agents. As in the previous method, the synthetic co-polymer "poly(lactide-glycolide)" is the preferred delivery vehicle for the nanospheres, however, as previous stated and outlined, other synthetic or natural biodegradable polymers could be used with varying results.

ALTERNATE METHOD OF CARRYING OUT THE INVENTION

Preparation of an alternate preferred embodiment of the invention is conducted as follows:

Stage One

An aqueous gel is prepared comprising a water-soluble polymer, such as polyvinyl alcohol, and a salting out agent, such as magnesium acetate tetrahydrate, dissolved in distilled water heated to 40° C. The water-soluble polymer and salting out agent are combined in the water in a 1:3 ratio, respectively. Polymer, comprising a predetermined ratio of poly(lactide-glycolide) co-polymer is dissolved (20% weight-to-weight) in a solution of acetone, or similar solvent, containing one or more dissolved drugs or active ingredients such as morphine sulfate (1%). A portion of the aqueous gel is added to the solvent/polymer/drug solution while the solution is being stirred vigorously with a high speed turbine propeller and while the solution is being maintained at a constant temperature of 40° C. A water-in-oil emulsion is thereby formed consisting of a liquid/liquid two phase system. The remainder of the aqueous gel is added to the solvent/polymer/drug solution under vigorous stirring with the turbine propeller and at a constant temperature of 40° C. This procedure results in the formation of an oil-in-water emulsion. Additional distilled water, at ambient temperature, is then added to the oil-in-water emulsion under constant, vigorous stirring in order to allow the diffusion of the acetone solvent into the aqueous phase. This procedure results in the formation of a solution containing drug-ladened, polymeric nanospheres. The solution is then decanted and filtered using vacuum filtration. The resulting product, microscopic nanospheres containing a homogenous matrix of morphine sulfate and co-polymer, is then washed a number of times with distilled water and placed in a vacuum oven for several hours for thorough drying and to remove any residual solvent.

Stage Two

A suppository base of Polyethylene glycol (PEG 8000) is melted in a constant temperature water bath. Once the PEG is in a molten state, the nanospheres produced in the previous stage are added while the suspension is being stirred with a glass rod. The nanospheres form a suspension with the PEG and the stirring action causes them to be evenly and homogeneously distributed throughout the PEG/nanosphere suspension. The molten PEG/nanosphere suspension is then poured into pre-heated metal molds for cooling and solidification. The resulting suppository preparation is allowed to cool and solidify at room temperature and the suppositories are then placed into storage at 4° C. As a result of this process, each suppository will contain approximately equal amounts of nanospheres containing equal amounts of active agent(s) such as morphine sulfate used in this example.

What is claimed is:

1. A four-stage, phased-release drug delivery means, comprising a suppository preparation comprising drug-ladened, polymeric synthesized microscopic particles within a pharmaceutically acceptable suppository base component wherein said microscopic particles have been specially formulated as a homogeneous matrix of active agent(s) and biodegradable polymers wherein the process for formulating said microscopic particles produces drug-ladened spheres no larger than 300 nanometers in diameter, the size and formulation of which allows these "nanoparticles" to be delivered, substantially intact, across the fenestrated capillaries of the rectal or vaginal mucosa for the controlled release of active agent(s) directly into the subject's systemic circulation; said four-stage, phased-release, delivery means comprising first, the delivery of the suppository containing said drug-ladened nanoparticle spheres into the rectal or vaginal cavity; second, the aquaous solubility of the chosen suppository base component; third, the uptake of said nanoparticle spheres into the fenestrated capillaries of the chosen cavity; and fourth, the release of active agent(s), controlled by the percentage composition of polymers used in the production of the nanoparticles, directly into the subject's systemic circulation.

2. The drug delivery means of claim 1, wherein said biodegradable polymers used in the production and formulation of said nanoparticle matrix is the co-polymer poly(lactide-glycolide).

3. The drug delivery means of claim 1, wherein said biodegradable polymers used in the production and formulation of said nanoparticle matrix are selected from the group of natural polymers consisting of serum albumins, collegen, gelatin, hemoglobin, polysaccharides, dexoyglucopyranose and celluloses.

4. The drug delivery means of claim 1, wherein the biodegradable polymers used in the production and formulation of said nanoparticle matrix are selected from the group of synthetic polymers consisting of poly(alkyl-a-cyanoacrylates), poly(amides), poly(acrylamide)-hydrogers, poly(orthoesters), poly(amino acids), poly(urethanes), polyacrylates/polymethacrylates, polyanhydrides, polyglycerol esters, polyhydroxybutyrate, polyhydroxyvalerate, poly-e-prolactone, polystyrene and co-polymers of styrene, polyethylenimine, polydimethyldiallylammonine chloride, glutamic acid—ethyl glutamate co-polymers, isocyanates, caboxyvinyl, polycritic acid, polymalic acid, poly-βhydroxybutric acid, poly-alkylene oxalates, poly-orthocarbonate/polycarbonates, silicone, maleic anhydride polymers, ethylene—vinyl acetate co-polymer, polyvinyl alcohol, polyacrylamide and other aliphatic polyesters such as poly(lactic acid), poly(glycolic acid), poly(ϵ-caprolactone), poly(hydroxy butyrate) and poly(hydroxy butyrate-co-valerate).

5. The drug delivery means of claim 1, wherein the percentage composition of polymers used in the production and formulation of said nanoparticle matrix is varied depending on the rate of dissolution desired for the controlled release of said active agent(s) within the subject's systemic circulation.

6. The drug delivery means of claim 1, wherein the suppository base component comprises a pharmaceutically acceptable form of polyethylene glycol.

7. The drug delivery means of claim 1, wherein the suppository base component is chosen from the group consisting of cocoa butter, glycerinated gelatin, hydrogenated vegetable oils, fatty acid esters of polyethylene glycols, glycolsurfactant PEGs, glycerinated gelatin, and nonionic surfactant materials such as polyoxyethylene derivatives of sorbitan monostearate and polyoxyl—40 stearate.

8. The drug delivery means of claim 2, wherein the percentage composition of lactide to glycolide of said co-polymer is varied depending on the rate of dissolution desired for the controlled release of said active agent(s) within the subject's systemic circulation.

* * * * *